United States Patent [19]

Berglund

[11] Patent Number: 4,459,265

[45] Date of Patent: Jul. 10, 1984

[54] AUTOMATICALLY OPERATING ANALYSIS APPARATUS

[75] Inventor: Erling Berglund, Järfälla, Sweden

[73] Assignee: Clinicon AB, Bromma, Sweden

[21] Appl. No.: 267,453

[22] Filed: May 27, 1981

[30] Foreign Application Priority Data

Jun. 25, 1980 [SE] Sweden ................................ 8004687

[51] Int. Cl.³ ...................... G01N 35/04; G01N 35/06
[52] U.S. Cl. ........................................ 422/64; 364/497; 364/499; 422/67; 422/100; 422/65; 436/47
[58] Field of Search ....................... 422/63, 64, 65, 66, 422/67, 100; 364/497, 498, 499

[56] References Cited

U.S. PATENT DOCUMENTS

| | | | |
|---|---|---|---|
| 3,432,271 | 3/1969 | Wasilewski | 422/66 |
| 3,728,079 | 4/1973 | Moran | 422/65 |
| 4,058,367 | 11/1977 | Gilford | 422/67 |
| 4,158,545 | 6/1979 | Yamashita et al. | 422/67 |
| 4,276,258 | 6/1981 | Ginsberg et al. | 422/67 |
| 4,311,667 | 1/1982 | Gocho | 422/100 |
| 4,315,891 | 2/1982 | Sakurada | 422/64 |

Primary Examiner—Michael S. Marcus
Attorney, Agent, or Firm—Browdy and Neimark

[57] ABSTRACT

An automatic clinical analysis apparatus for liquid samples includes a stepwise rotatable circular plate which carries a plurality of reaction tubes on the periphery thereof; and at least one, and preferably several, reagent supply stations arranged at mutually different locations around said plate. The stations are operative to supply reagent liquid to the reaction tubes carried by said plate; a sample supply station is operative to supply sample liquid to said tubes carried by said plate; and a measuring station in which liquid can be withdrawn from said tubes by suction and analytically measured. The sample supply station is able to supply sample liquid selectively from any one of a large number of sample containers to that reaction tube in the plate which has been advanced to a given position. Each reagent supply station is able to supply any one of a plurality of mutually different reagent liquids to any one of two different reaction tubes in said rotary plate located at different given positions. The rotary plate may be arranged to move each reaction tube through a number of revolutions prior to withdrawing liquid therefrom at the measuring station. In this way the sample liquid can be supplied selectively at different moments in time prior to carrying out the measuring process, and several different reagent liquids, or combinations thereof, can be selectively supplied to the sample at different, selected moments in time, prior to carrying out said measuring process.

22 Claims, 3 Drawing Figures

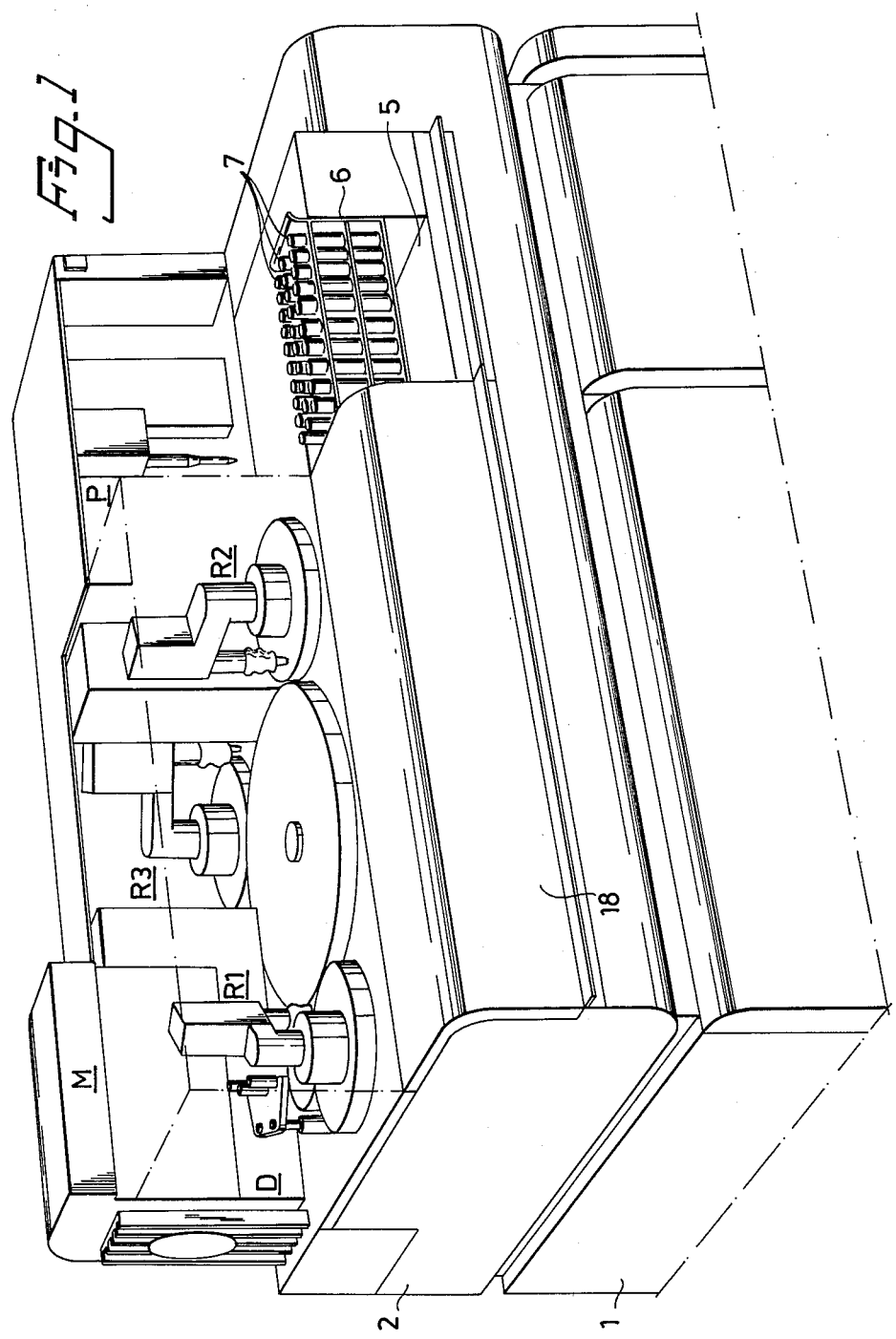

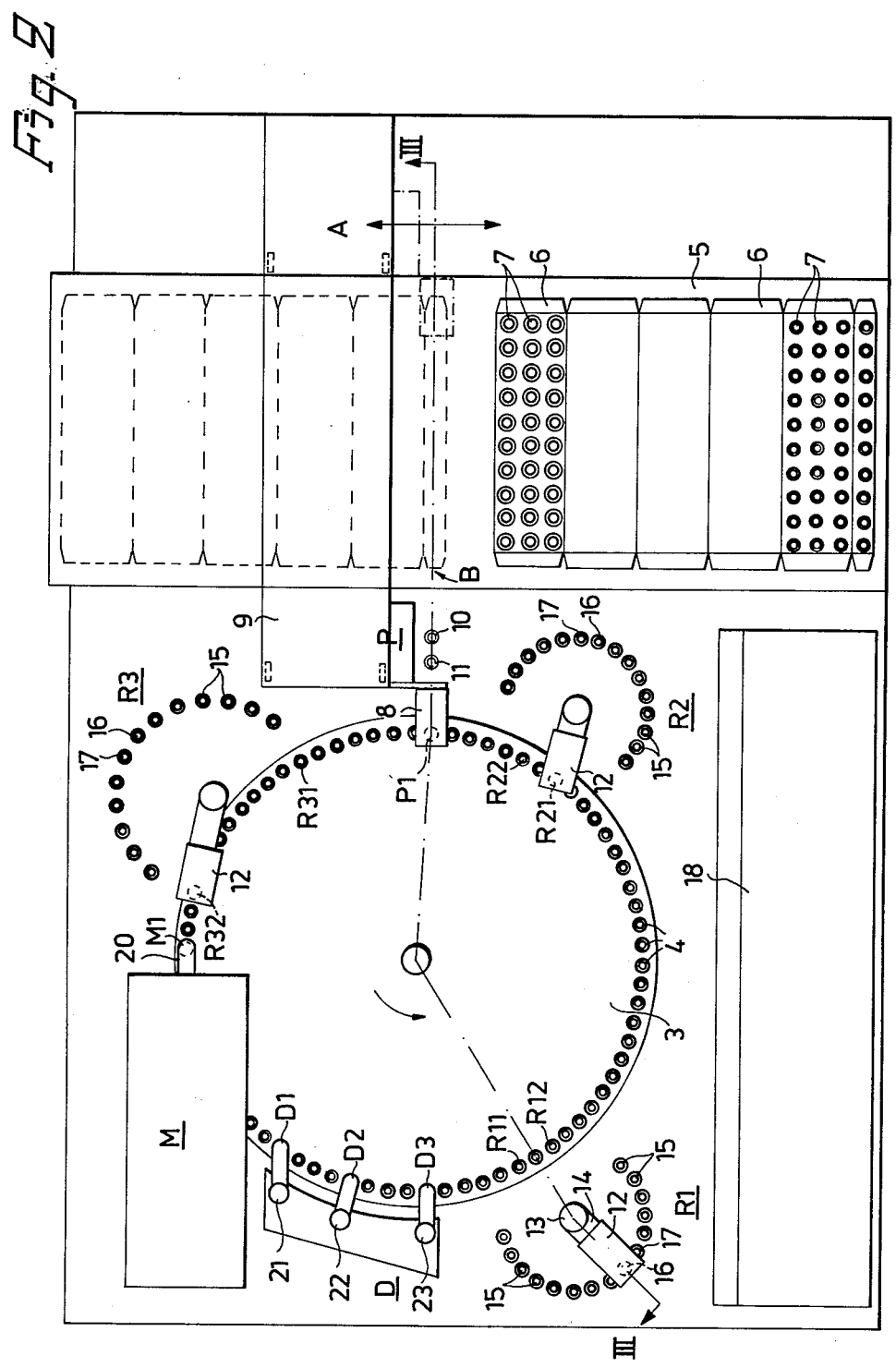

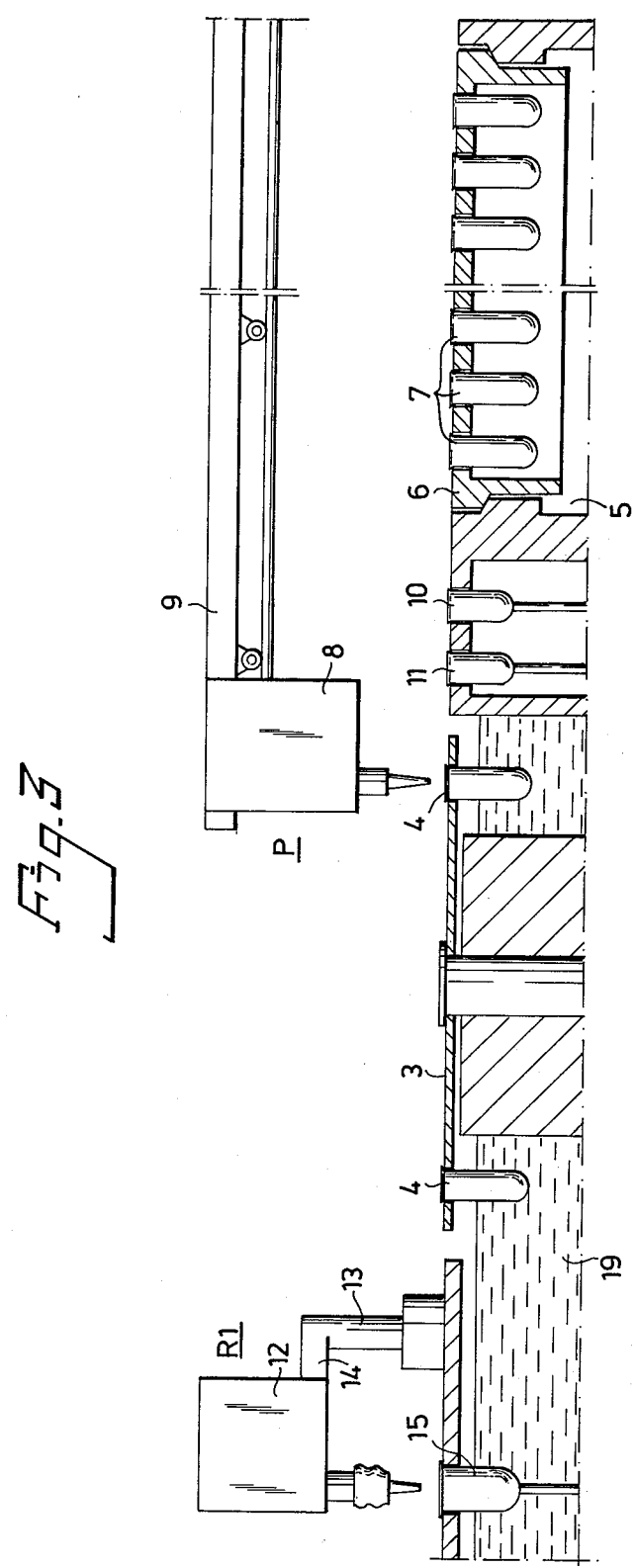

AUTOMATICALLY OPERATING ANALYSIS APPARATUS

The present invention relates to an automatically operating apparatus for analysing liquid samples, particular for determining the presence of different biochemical substances in biological liquid samples, such as blood serum.

In modern day medical care a large number of various samples of differing kinds are taken from patients and analysed with respect to different properties of the samples. The number of samples which must be taken in the care of these patients is very high and is constantly increasing, and hence there is a need for automatically operating clinical analysing apparatus capable of carrying out different analyses on a large number of different samples. A common feature of many of such analyses is that certain reagent liquids, buffer liquids and/or diluting liquids, all hereinafter referred to under the general term "reagent liquids", must be added to the original sample, and that, subsequent to the addition of these reagent liquids, the sample must be maintained at a controlled temperature for a predetermined holding time before being subjected to an analytical measuring process, by means of a photometer for example, thereby to determine the presence in the original sample of a given biochemical substance for example. The reagent liquids added to the sample and the concentrations in which said liquids are present therein, and the holding time prior to carrying out the analytic measuring operations vary for different analyses, e.g. independence upon which biochemical substance in the original sample is to be determined. Those automatically operating clinical analysis apparatus available today can be divided substantially into two categories. One type of automatically operating clinical analysis apparatus is the so-called parallel-operating apparatus which comprises a plurality of different, parallel, simultaneously operating process channels, each of which is arranged to carry out a respective specific analysis, i.e. to determine the presence of a specific biochemical substance. The different samples are supplied to the apparatus sequentially and each sample is automatically divided into part samples, each of which is dispatched to a respective process channel in accordance with those specific analyses to be carried out on the sample in question, said sample normally being labelled by means of a suitable code on the sample container. Although such a parallel-operating analysis apparatus has a very high capacity when required to carry out a relatively large number of analyses, the apparatus becomes very bulky and complicated, and therewith expensive. Since the number of parallel process channels incorporated in the apparatus is, of necessity, limited, it is only possible, despite all, to carry out a relatively limited number of different analyses, without requiring the different process channels to be re-set with respect to the reagent liquids supplied thereto and to the sample reaction times. This re-setting of a process channel for carrying out a different analysis to a previous one requires the use of further personnel and is relatively time consuming.

Another type of automatically operating clinical analysis apparatus is the so-called series-operating apparatus. Such an apparatus comprises only one single process channel, arranged to carry out a single specific analysis. The samples are supplied to the apparatus in sequence and are sequentially subjected to the specific analysis for which the apparatus is intended. Such a series-operating analysis apparatus is of relatively simple construction and is inexpensive and requires but a relatively small space. The capacity of such an apparatus, however, is low and the apparatus is only able to carry out one single specific analysis on all the samples supplied thereto. If the samples are to be subjected to a different analysis, it is necessary to re-set the apparatus for that particular analysis. This means that if a sample is to be subjected to a plurality of differing analyses, it is necessary to first divide the sample into a number of part samples, which are supplied to the apparatus at different occasions, and to re-set the apparatus each time an analysis which is different from the preceding analysis is to be made. Thus, such an apparatus requires comprehensive handling of the samples before said samples are supplied to the apparatus, and the apparatus must be re-set manually a repeated number of times. One known apparatus of this principle kind is described, for example, in the U.S. Pat. No. 3,758,274.

The object of the present invention is to provide an automatically operating clinical analysis apparatus which is relatively inexpensive and of simple construction and requires but a relatively small space and can be programmed to carry out a large number of different analyses on a larger number of samples which are supplied to the apparatus simultaneously.

With this object the invention provides an automatically operating analysis apparatus, which comprises stepwise drivable conveyor means arranged to move a plurality of reaction tubes, arranged sequentially in the feed direction of said conveyor means, stepwise in a closed circuit-path, at least one reagent-supply station and a measuring station situated at separate locations around said circuit-path, said reagent-supply station including means operative to supply reagent liquid to one of said reaction tubes when the tube is moved by said conveyor means into a given position relative said reagent supply station, and said measuring station including means for withdrawing liquid by suction from one of said reaction tubes when the tube is moved by said conveyor means into a given position relative said measuring station and for measuring said liquid analytically, and which is characterized in that said apparatus further comprises a sample supply station which is arranged at a given location along the circuit-path of the conveyor means and which includes means operative to supply a liquid sample to one of said reaction tubes when the tube is moved by said conveyor means into a given position relative said sample supply station; and in that said means of the reagent supply station is operative to selectively supply one each of a plurality of different reagent liquids to the reaction tube moved into said given position relative the reagent supply station.

In a preferred embodiment of the apparatus according to the invention, the apparatus comprises a plurality of reagent supply stations arranged at different locations along the circuit-path of the conveyor means, and each of said reagent supply stations is capable of supplying reagent liquid selectively to either one of two different reaction tubes moved by the conveyor means into two different positions relative the reagent supply station.

In a particular preferred embodiment of the apparatus according to the invention the sample supply station is operative to supply selectively any one of a plurality of different liquid samples to the reaction tube which is moved by the conveyor means into a given position relative the sample supply station.

Because the analysis apparatus according to the invention comprises one or preferably a plurality of reagent-supply stations, each of which can selectively supply a plurality of different reagent liquids to a reaction tube which can be advanced to a given position relative to the reagent-supply station by means of the stepwise drivable conveyor means, for example a stepwise rotatable turntable, it is possible to supply to each separate sample a large number of different reagent liquids and combinations thereof, thereby enabling the apparatus to carry out a large number of different analyses, by programming the reagent-supply stations to select a reagent liquid in dependence upon the desired analysis. Since each reagent-supply station only requires a single metering pump, the apparatus is of relatively simple construction and inexpensive, despite the large number of different analyses which can be carried out.

Because, in a particularly advantageous embodiment of the invention, each reagent-supply station is able to supply reagent liquid selectively to each of two different reaction tubes transported by the conveyor means, and because said conveyor means is controlled to move each tube through a plurality of full revolutions before the contents of the tube are withdrawn therefrom at the measuring station in which the measuring operation is carried out, it is possible to select a plurality of different times at which the different reagent liquids are supplied to a respective tube, and also to select different times for supplying the sample itself in relation to the time at which the analytical measurement is carried out in said measuring station. This further increases the possibility of carrying out a plurality of different analyses.

Because in the particularly preferred embodiment of the invention the sample-supply station is arranged to selectively supply any one of a plurality of different samples present in the apparatus to that reaction tube which is advanced to the sample-supply station by means of the conveyor means, it is possible by means of the apparatus to automatically and selectively carry out a large number of different analyses on a large number of different samples introduced into the apparatus at the same time. Thus, each sample can be subjected to all of the different analyses for which the apparatus is programmed, in any desired combination, without it being necesary to divide the samples into part samples before introducing them into the apparatus and without the apparatus needing to be re-set manually in accordance with the different analyses to be carried out. In this respect, the apparatus can be programmed to carry out a given analysis on all those samples to which said given analysis applies, thereafter the apparatus is automatically re-set to carry out another analysis on all those samples to which said other analysis applies, etc., etc. This mode of operation enables the total number of samples to be analysed quickly, with a minimum number of re-settings of the apparatus between the different analyses, whereat it shall be observed that these re-settings are made automatically by the apparatus. The apparatus, however, can also be programmed, to no disadvantage, to treat the samples introduced thereto in a given sequence and to carry out on each sample in turn all analyses applicable to the sample in question. The samples are treated more slowly with this mode of operation, since it is necessary to re-set the apparatus a large number of times. This mode of operation, however, can be advantageous when the samples are not introduced to the apparatus simultaneously in a large number, but are introduced thereto one at a time or in a relatively small number at different occasions.

An advantageous embodiment of the invention will now be described with reference to the accompanying drawing, in which FIG. 1 illustrates schematically and in perspective the upper part of an analysing apparatus according to the invention, the figure illustrating those parts of the apparatus which are of interest with respect to the invention, namely the stepwise drivable conveyor means for the reaction tubes; the sample-supply station for selectively supplying different samples to the reaction tubes; the different reagent-supply stations for selectively supplying the different reagent liquids to the reaction tubes; the measuring station for withdrawing liquid from the reaction tubes by suction and for carrying out an analytical measurement on said liquid; and a washing station for washing the reaction tubes subsequent to liquid being withdrawn therefrom and passed to the measuring station;

FIG. 2 is a schematic top plan view of the analysis apparatus illustrated in FIG. 1; and FIG. 3 is a schematic view of the upper part of the analysis apparatus taken on the line III—III in FIG. 2.

The drawing illustrates schematically a preferred embodiment of an analysis apparatus according to the invention, only those parts which are of primary interest with respect to the invention being shown. Thus, the drawing does not illustrate those mechanical and electrical components required for driving and controlling the reaction-tube conveyor means, the metering pumps at the sample-supply station and the different reaction-supply stations; the various elements of the washing station and the sample-container holders containing the original samples. Neither does the drawing illustrate in detail the construction of the measuring station at which the analytical measurements are taken, nor yet the programming means for programming the different operating sequences of the control means and for processing, storing and presenting the analysis results obtained. All of these elements of an analysis apparatus constructed in accordance with the invention may have any known, conventional form, which can readily be realized by one of normal skill in the art having knowledge of the information hereinafter given with regard to the desired mode of operation of the various components in an analysis apparatus according to the invention for treating the samples in the manner intended.

The illustrated embodiment of an analysing apparatus according to the invention comprises a cabinet 1 which houses at least some of the aforementioned, not shown components of the analysing apparatus. The cabinet 1 has an upper part 2 which houses all of the devices and elements required for handling and treating the samples in accordance with the invention. Arranged on top of said upper part 2 is a turntable 3 which is arranged for stepwise rotation about a vertical axis, in a manner described hereinafter in more detail. Arranged around the periphery of the turntable 3 is a plurality of uniformly spaced reaction tubes 4; in the illustrated embodiment there are 75 such tubes. The turntable 3 can be rotated stepwise through an arc equal to the angle subtended by two mutually adjacent tubes 4, or equal to a plurality of such angles as will be described in more detail hereinafter. Thus, around the turntable 3 are 75 fixed positions to which each tube 4 can be advanced, by stepwise rotation of the turntable 3. The turntable 3 functions as a stepwise drivable conveyor means, operative to advance the reaction tubes 4 stepwise in a closed path.

On the right of the upper part 2, as seen in FIG. 1, there is arranged a recess 5 in which a rack 6 for test tubes 7 can be placed. Each rack 6 can carry a plurality of test tubes 7 arranged in mutually parallel rows. As shown in FIG. 2, each rack 6 may carry, for example, three rows each comprising ten test tubes 7. It will be understood, however, that racks capable of carrying a smaller or a greater number of rows of test tubes can be used. The recess 5 is capable of accomodating a plurality of racks 6, for example five racks each carrying thirty test tubes, thereby enabling a total of 150 test tubes, each containing a respective sample, to be introduced into the apparatus. Co-operating with the recess 5 are elements (not shown) arranged to engage the racks 6 in a manner such that under the action of a control means (not shown) said racks can be moved backwards and forwards in the recess 5, in the direction of the arrow A, thereby enabling any selected row of test tubes 7 to be brought into a position marked B located opposite a sample-supply station generally shown at P.

Arranged in the sample-supply station P is a pipette or metering pump 8, which is arranged to be moved by means of a carriage 9 with associated drive and control means, rectiliniary along that row of test tubes 7 located at position b, and also to that reaction tube 4 in the turntable 3 which at that moment is located opposite the sample-supply station in the position P1 shown in FIG. 2. The metering pump 8 can be selectively stopped above each of the test tubes 7 in the row of test tubes located in position B, and also above the reaction tube 4 in the position P1. The metering pump is arranged to be lowered down into said test tube 7, for withdrawing sample liquid therefrom by suction, and to dispense an accurately determined volume of said sample liquid to the reaction tube 4 in the position P1. Consequently, by programming the control of the metering pump 8 and the racks 6, it is possible to cause the metering pump 8 to transfer sample liquid from any of the test tubes 7 present in the apparatus to that reaction tube 4 which is located at that moment in said position P1. A metering pump which can be used for this purpose is described in European Patent Application No. 79 850080-7.

The sample-supply station P also includes a stationary cup 10 arranged to constantly contain a suitable washing liquid, for example plain water, and a stationary outlet cup or drain 11. The metering pump 8 can be controlled so as to also stop above the cups 10 and 11, thereby to enable the pump to withdraw washing liquid from the cup 10 and then to dispense said liquid to the outlet cup 11. In this way it is possible to cleanse the metering pump 8 between the stages of transferring different samples from the tubes 7 to the tubes 4 in the turntable 3, thereby preventing mutual contamination of the samples.

Arranged around the turntable 3 are three reagent-supply stations, generally shown at R1, R2 and R3 respectively. These reagent-supply stations are principally all of the same design, and hence only one station, R1, will be described. Arranged in the station R1 is a pipette or metering pump 12 which is carried by means of an arm 14 extending from a post 13, such that said pump can be rotated in a circular path around the post 13. In principle, the metering pump 12 may be of the same design as the metering pump 8 in the sample-supply station P. Arranged around the circular movement path of the metering pump 12 is a plurality of stationary cups 15 for mutually different reagent liquids, the number of said cups being 13 in the illustrated embodiment. The circular movement path of the metering pump 12 is also arranged to pass over those two tubes 4 in the turntable 3 which are located at the positions marked R11 and R12 in FIG. 2. Thus, by programming the control of the movement of the pump 12, the pump can be caused to withdraw reagent liquid from any of the 13 reagent cups 15 and to deliver this liquid in an accurately determined volume to any of the tubes 4 located at the positions R11 and R12. Arranged along the circular movement path of the pump 12 is a stationary cup 16 for washing liquid, for example water, and a stationary cup 17 which serves as a drain, thereby enabling the pump 12 to be washed clean between the handling of different reagent liquids, in a manner similar to that previously described with reference to the sample-supply pump 8. This prevents mutual contamination of the different reagent liquids.

In a corresponding manner, the pump 12 in the reagent-supply station R2 can be caused to supply any one of the reagent liquids in the 13 reagent cups 15 to any one of those tubes 4 carried by the turntable 3 which is at that moment located in positions R21 and R22 in FIG. 2. The reagent-supply station R3 only has eleven reagent cups 15 and the metering pump 12 of said station R3 can be caused to supply reagent liquid from any one of said reagent cups to any one of the two reaction tubes 4 located at that moment in the two positions R31 and R32 in FIG. 2.

The reagent liquids may be supplied to the various reagent cups 15, for example, in the manner described in the Swedish Patent Application No. 8001913-6, said liquids being taken from storage flasks positioned in a particular space 18 which is closed with a lid and located in the forward part of the upper part 2 of the apparatus. This space 18 can be cooled so as to extend the durability of the reagent liquid, while the reagent cups 15 and the reaction tubes 4 in the turntable 3 are arranged to be immersed in a temperature-controlling bath 19 (see FIG. 3) to enable the reagent liquids in the cups 15 and the samples in the tubes 4 to be maintained at a temperature suitable for the analysis reaction.

It will be understood from the aforegoing that by means of the three reagent-supply stations R1, R2 and R3 a total of 37 mutually different reagent liquids can be supplied to each tube 14 in the turntable 3 on a total of six different occasions during one full rotation of the table 3, said table being assumed here to rotate in the direction of the arrow C.

Also arranged on the upper part 2 of the analysing apparatus is a measuring station M which incorporates at least one suction pipe 20 arranged to be introduced into that tube 4 in the turntable 3 which at that moment is located in the position marked M1 in FIG. 2, for withdrawing liquid by suction from said tube, so that the desired analysis measurement can be carried out at said measuring station. The measuring station may have any desired, suitable construction, comprising for example a photometer. If the time required to carry out a measuring operation in the measuring station M is longer than that corresponding to the rate at which further tubes 4 are advanced to the position M1 by the turntable 3, the measuring station M can, to advantage, be provided with a plurality of parallel, simultaneously operating process channels, in which different samples withdrawn sequentially from different reaction tubes 4 are treated. In this case the measuring station M is suitably provided with a corresponding number of suction pipes 20.

Arranged between the measuring station M and the reagent-supply station R1 is a washing station D, in which those reaction tubes 4 from which liquid has just been withdrawn by suction at the measuring station M can be washed. The washing station D comprises first means 21 arranged to introduce a suction pipe into the tube 4 located in the position D1, for emptying said tube of any liquid remaining therein; second means 22 arranged to introduce a rinsing pipe in the tube 4 located in the position D2 for rinsing said tube with rinsing liquid, for example plain water; and third means 23 arranged to introduce an air pipe into the tube 4 located in position D3 for blowing air into said tube, to dry the same.

Driving of the turntable 3 can be so controlled that said table is rotated in steps each of which equals an arc which includes the angle subtended by two adjacent tubes 4, and the measuring station M is controlled to withdraw liquid from each tube 4 each time said each tube takes the position M1. In this way, as previously mentioned, any selected tube 4 may be supplied with a number of different reagent liquids at different times corresponding to positions R11, R12, R21, R22, R31 and R32, and sample liquid is supplied at that point of time corresponding to position P1. The reaction times in question will be determined by the rate at which the turntable 3 is indexed.

The turntable 3 and the measuring station M, however, can be controlled in a manner such that subsequent to withdrawing liquid from a tube 4 in the measuring station M, said tube is moved through a plurality of revolutions before liquid is withdrawn therefrom again. This provides a still greater number of possible occasions on which the various reagent liquid can be supplied to respective tubes and when said sample liquid can be supplied thereto, thereby providing a greater possibility of selecting desired reaction times in accordance with the specific analysis to be carried out.

To reduce the number of times at which the turntable 3 must be started and stopped, such start and stop periods reducing the time available for supplying samples and reagent liquids to the tubes 4, it may be to advantage to arrange for the turntable to be driven in a manner such that at least certain of the indexing steps equal an angle of arc which includes a plurality of tubes and so that each tube 4 takes each of the reagent-supply positions R11, R12, R21, R22, R31 and R32 and the sample-supply position P1 and also the washing positions D1, D2 and D3 at least once, and to advantage a number of times, during the number of revolutions through which the tube 4 is moved by means of the table 3 between those times at which liquid is withdrawn from a tube 4 in question at the position M1 of the measuring station M. In the illustrated embodiment, the turntable 3 can be controlled so as to execute a feed step which includes alternately one angular division and three angular divisions respectively between adjacent tubes, and to move each tube 4 through four full revolutions of the turntable between each subsequent withdrawal operation at the measuring position M1. Thus, two sequential feed steps will include four angular divisions, and hence the turntable 3 will execute 150 feed steps in the course of four full revolutions. In this way, each tube 4 will pass through the sequence illustrated in the table below. The table shows in the left hand column information concerning the number of different fixed positions, whereat the position M1 of the measuring station is numbered 0 and the numbering extending in the direction of rotation C of the turntable 3. The left hand column also contains information concerning the different working positions of the various units, i.e. the reagent-supply stations R1, R2 and R3, the sample-supply station P, the washing station D and the measuring station M. Each of the four remaining columns shows a respective one of the four revolutions for the complete sequence, and each of said columns contains information concerning the number of feed steps carried out by the turntable 3 and the time remaining in minutes and seconds after each feed step until the withdrawal of liquid at the measuring position M1 (position No. 0) from the tube 4 in question. Those measuring steps and times respectively at which the unit marked in the left hand column is able to carry out a working operation with respect to the tube 4 in question are framed in the said four columns.

| Fixed Posit. No. | Unit/Pos. | Rotation 1 | | Rotation 2 | | Rotation 3 | | Rotation 4 | |
|---|---|---|---|---|---|---|---|---|---|
| | | After Step No. | Time to meas | After Step No. | Time to meas | After Step No. | Time to meas | After Step No. | Time to meas |
| 1 | | 1 | 12.25 | 38 | 9.20 | | | | |
| 2 | | | | 39 | 9.15 | 76 | 6.10 | | |
| 3 | | | | | | 77 | 6.05 | 114 | 3.00 |
| 4 | | 2 | 12.20 | | | | | 115 | 2.55 |
| 5 | | 3 | 12.15 | 40 | 9.10 | | | | |
| 6 | | | | 41 | 9.05 | 78 | 6.00 | | |
| 7 | | | | | | 79 | 5.55 | 116 | 2.50 |
| 8 | | 4 | 12.10 | | | | | 117 | 2.45 |
| 9 | | 5 | 12.05 | 42 | 9.00 | | | | |
| 10 | | | | 43 | 8.55 | 80 | 5.50 | | |
| 11 | | | | | | 81 | 5.45 | 118 | 2.40 |
| 12 | WASH./D1 | 6 | 12.00 | | | | | 119 | 2.35 |
| 13 | | 7 | 11.55 | 44 | 8.50 | | | | |
| 14 | | | | 45 | 8.45 | 82 | 5.40 | | |
| 15 | | | | | | 83 | 5.35 | 120 | 2.30 |
| 16 | WASH./D2 | 8 | 11.50 | | | | | 121 | 2.25 |
| 17 | | 9 | 11.45 | 46 | 8.40 | | | | |
| 18 | | | | 47 | 8.35 | 84 | 5.30 | | |
| 19 | | | | | | 85 | 5.25 | 122 | 2.20 |
| 20 | WASH./D3 | 10 | 11.40 | | | | | 123 | 2.15 |
| 21 | | 11 | 11.35 | 48 | 8.30 | | | | |
| 22 | | | | 49 | 8.25 | 86 | 5.20 | | |
| 23 | | | | | | 87 | 5.15 | 124 | 2.10 |

-continued

| Fixed Posit. No. | Unit/Pos. | Rotation 1 | | Rotation 2 | | Rotation 3 | | Rotation 4 | |
|---|---|---|---|---|---|---|---|---|---|
| | | After Step No. | Time to meas | After Step No. | Time to meas | After Step No. | Time to meas | After Step No. | Time to meas |
| 24 | | 12 | 11.30 | | | | | 125 | 2.05 |
| 25 | REAG.R1/R11 | 13 | 11.25 | 50 | 8.20 | | | | |
| 26 | | | | 51 | 8.15 | 88 | 5.10 | | |
| 27 | REAG.R1/R12 | | | | | 89 | 5.05 | 126 | 2.00 |
| 28 | | 14 | 11.20 | | | | | 127 | 1.55 |
| 29 | | 15 | 11.15 | 52 | 8.10 | | | | |
| 30 | | | | 53 | 8.05 | 90 | 5.00 | | |
| 31 | | | | | | 91 | 4.55 | 128 | 1.50 |
| 32 | | 16 | 11.10 | | | | | 129 | 1.45 |
| 33 | | 17 | 11.05 | 54 | 8.00 | | | | |
| 34 | | | | 55 | 7.55 | 92 | 4.50 | | |
| 35 | | | | | | 93 | 4.45 | 130 | 1.40 |
| 36 | | 18 | 11.00 | | | | | 131 | 1.35 |
| 37 | | 19 | 10.55 | 56 | 7.50 | | | | |
| 38 | | | | 57 | 7.45 | 94 | 4.40 | | |
| 39 | | | | | | 95 | 4.35 | 132 | 1.30 |
| 40 | | 20 | 10.50 | | | | | 133 | 1.25 |
| 41 | | 21 | 10.45 | 58 | 7.40 | | | | |
| 42 | | | | 59 | 7.35 | 96 | 4.30 | | |
| 43 | | | | | | 97 | 4.25 | 134 | 1.20 |
| 44 | | 22 | 10.40 | | | | | 135 | 1.15 |
| 45 | | 23 | 10.35 | 60 | 7.30 | | | | |
| 46 | | | | 61 | 7.25 | 98 | 4.20 | | |
| 47 | | | | | | 99 | 4.15 | 136 | 1.10 |
| 48 | | 24 | 10.30 | | | | | 137 | 1.05 |
| 49 | REAG.R2/R21 | 25 | 10.25 | 62 | 7.20 | | | | |
| 50 | | | | 63 | 7.15 | 100 | 4.10 | | |
| 51 | REAG.R2/R22 | | | | | 101 | 4.05 | 138 | 1.00 |
| 52 | | 26 | 10.20 | | | | | 139 | 0.55 |
| 53 | | 27 | 10.15 | 64 | 7.10 | | | | |
| 54 | | | | 65 | 7.05 | 102 | 4.00 | | |
| 55 | | | | | | 103 | 3.55 | 140 | 0.50 |
| 56 | SAMPLE P/P1 | 28 | 10.10 | | | | | 141 | 0.45 |
| 57 | | 29 | 10.05 | 66 | 7.00 | | | | |
| 58 | | | | 67 | 6.55 | 104 | 3.50 | | |
| 59 | | | | | | 105 | 3.45 | 142 | 0.40 |
| 60 | | 30 | 10.00 | | | | | 143 | 0.35 |
| 61 | | 31 | 9.55 | 68 | 6.50 | | | | |
| 62 | | | | 69 | 6.45 | 106 | 3.40 | | |
| 63 | REAG.R3/R31 | | | | | 107 | 3.35 | 144 | 0.30 |
| 64 | | 32 | 9.50 | | | | | 145 | 0.25 |
| 65 | | 33 | 9.45 | 70 | 6.40 | | | | |
| 66 | | | | 71 | 6.35 | 108 | 3.30 | | |
| 67 | | | | | | 109 | 3.25 | 146 | 0.20 |
| 68 | | 34 | 9.40 | | | | | 147 | 0.15 |
| 69 | | 35 | 9.35 | 72 | 6.30 | | | | |
| 70 | | | | 73 | 6.25 | 110 | 3.20 | | |
| 71 | | | | | | 111 | 3.15 | 148 | 0.10 |
| 72 | REAG.R3/R32 | 36 | 9.30 | | | | | 149 | 0.05 |
| 73 | | 37 | 9.25 | 74 | 6.20 | | | | |
| 74 | | | | 75 | 6.15 | 112 | 3.10 | | |
| 0 | MEAS.M/M1 | | | | | 113 | 3.05 | 150 | 0.00 |

As will be seen from the table, the tube 4 is washed initially at positions No. 12 (D1), No. 16 (D2) and No. 20 (D3), after the sixth, eighth and tenth feed steps respectively. It will also be seen that reagent liquid can be supplied to the tube 4 from the reagent-supply station R1 on four different occasions, namely after feed steps 13, 50, 89 and 126. In a similar manner, reagent liquid can be supplied to the tube from the reagent-supply station R2 on four different occasions, namely after feed steps 25, 62, 101 and 138. Reagent liquid can also be supplied from the reagent-supply station R3 or four different occasions, namely after feed steps 36, 107, 144 and 149. Sample liquid can be supplied to the tube 4 from the sample-supply station P on two different occasions, namely after feed steps 28 and 141. It will be seen that by programming the control of the sample-supply station P and the three reagent-supply stations R1, R2, R3, it is possible to carry out a large number of different analyses. In the table it has been assumed that the time interval between two sequential feed steps is five seconds; although it will be understood that other time intervals can be selected if so desired. Neither it is necessary for the time interval between sequential feed steps always to be the same.

It will also be understood that an automatically operating analysing apparatus according to the invention can be modified and designed in a number of different ways, to suit the intended purpose. Thus, for example, the number of different reagent-supply stations may be varied, as can also their mutual positions, and their positions relative to the positions of the sample-supply stations. The number of different possible reagent liquids in each reagent-supply station may also be varied. Neither is it necessary for all reagent-supply stations to be able to supply reagent liquid to two different reaction tubes 4 in the turntable 3, even though this provides a greater degree of selectivity. It will also be understood that the number of tubes 4 in the turntable 3, and the indexing pattern of said turntable, can also be varied to suit different purposes.

In the described and illustrated embodiment, the reaction tubes are moved stepwise in a circular path by means of the turntable 3, this arrangement providing a relatively simple construction. It will be understood, however, that other conveying means may be used for moving the reaction tubes. Thus, there may be used an endless, stepwise drivable conveyor chain or like element. The path along which the tubes move need not therewith be circular, which in certain cases may be an advantage. By changing a conveyor chain it will therewith be possible to change the length of the movement path and/or the shape of said path and also to change the number of tubes present in said path.

As will also be understood, an apparatus constructed in accordance with the invention may also include further process stations along the path travelled by the reaction tubes, for example, stations in which the contents of the tubes are agitated. Such an agitating station may have the form, for example, of that described in Swedish Patent Application No. 80 01912-8.

I claim:

1. An automatically operating analysis apparatus for analysing liquid samples, comprising a rotatable turntable;

a plurality of reaction tubes carried by said turntable and means to uniformly space said tubes around the periphery of said turntable;

drive means for stepwise rotation of said turntable through rotation steps each equal to a whole number of the angular spacing between two adjacent reaction tubes;

a sample supply station, at least a first reagent supply station and a measuring station, means to locate said sample supply, said first reagent supply and said measuring station at separate locations around the periphery of said turntable;

said sample supply station including holder means for holding a plurality of sample containers for a respective liquid sample each and sample transfer means operative to transfer a liquid sample selectively from any one of said sample containers to one of said reaction tubes moved by said turntable into a given position relative the sample supply station;

said first reagent supply station including a plurality of stationary reagent cups for a respective reagent liquid each and reagent transfer means operative to transfer reagent liquid selectively from any one of said reagent cups to one of said reaction tubes which is moved by said turntable into a given position relative said first reagent supply station, said reagent transfer means including a metering pump having a suction tube operative to draw liquid into said suction tube by suction and to dispense said liquid in an accurately determined volume, means to controllably move said suction tube to positions above said reagent cups for selective removal by suction of reagent liquid from any one of said cups and to controllably move said suction tube to said given position above a reaction tube moved by said turntable for dispensing reagent liquid into said tube;

said measuring station including measuring means for analytically measuring a given property of a sample held in one of said reaction tubes which is moved by said turntable into a given position relative said measuring station;

means to control said drive means for said turntable and said measuring means of said measuring station so that each reaction tube is moved by said turntable through a plurality of complete turns of the turntable before the liquid present in said reaction tube is subjected to an analytic measuring operation by said measuring means and so that each reaction tube during said plurality of complete turns of said turntable is at least twice brought into a position relative to said sample supply station and each said reagent supply station respectively, to permit sample liquid and reagent liquid, respectively, to be transferred to said reaction tube, said control means also permitting said sample supply station and each said reagent supply station to transfer sample liquid and reagent liquid, respectively, to each separate reaction tube at at least two different occasions prior to liquid in said reaction tube being subjected to a measuring operation in said measuring station.

2. An apparatus as claimed in claim 1, further comprising additional reagent supply stations each similar in design to said first reagent supply station, and means to locate each said additional supply station at different locations around the periphery of said turntable.

3. An apparatus as claimed in claim 1, means to locate said at least one reagent supply station after said sample supply station but before said measuring station as seen in the direction of rotation of said turntable, and means to locate at least one other reagent supply station before said sample supply station but after said measuring station as seen in the direction of rotation of said turntable.

4. An apparatus as claimed in claim 1, means to selectively move said suction tube of said metering pump in said reagent supply station to a position above either one of two different reaction tubes moved by said turntable into two different given positions relative to the reagent supply station for dispensing reagent liquid into either one of said two reaction tubes.

5. An apparatus as claimed in claim 1, wherein said reagent supply station also includes a stationary wash cup for a washing liquid and a stationary waste outlet, means to controllably move said suction tube of said metering pump to a position above said wash cup for withdrawing liquid therefrom by suction and to controllably move said suction tube to a position above said waste outlet for emptying the contents of the pump thereinto.

6. An apparatus as claimed in claim 1, and means to move said suction tube of said metering pump in said reagent supply station in a circular path.

7. An apparatus as claimed in claim 1, wherein said rotational steps of said turntable correspond alternatingly to m and n angular spacings between two adjacent reaction tubes, where m and n are different whole numbers, and the number of said reaction tubes is not divisible by the sum $m+n$.

8. An apparatus as claimed in claim 1, wherein said measuring station includes suction means for withdrawing liqud from a said reaction tube when moved by said turntable into said given position relative the measuring station and for transferring said withdrawn liquid to said measuring means, and said measuring means comprising several independent, sequentially operative measuring channels to which liquids withdrawn by said suction means from reaction tubes moved sequentially into said given position are transferred.

9. An apparatus as claimed in claim 1, wherein said sample transfer means in said sample supply station includes a metering pump having a suction tube operative to draw liquid into said suction tube by suction and to dispense said liquid in an accurately determined volume, means to controllably move said suction tube to positions above said sample containers for selective removal by suction of sample liquid from any one of said sample containers and to controllably move said suction tube to said given position relative the sample supply station above a reaction tube moved by said turntable for dispensing said withdrawn liquid sample to said reaction tube.

10. An apparatus as claimed in claim 9, wherein said sample supply station also includes a stationary wash cup for a washing liquid and a stationary waste outlet, means to controllably move said suction tube of said metering pump to a position above said wash cup for withdrawing liquid by suction therefrom and to a position above said waste outlet for emptying its contents into said waste outlet.

11. An apparatus as claimed in claim 1, and means to move said suction tube of said metering pump in said sample supply station in a rectilinear path, along which rectilinear path said sample containers are located.

12. An apparatus as claimed in claim 11, wherein said holder means comprise means for holding a plurality of rows of sample containers extending mutually parallel and parallel with the path of movement of said suction tube, and means to controllably move said holder means in a manner such as to selectively place any one of said rows of sample containers in alignment with the path of movement of said suction tube.

13. An apparatus as claimed in claim 1, a washing station, means to locate said washing station at the periphery of said turntable after said measuring station as seen in the direction of rotation of said turntable and before said reagent supply station, said washing station including means for washing each reaction tube as it passes said washing station for the first time subsequent to the liquid contained in the reaction tube having been subjected to a measuring operation in said measuring station.

14. An apparatus as claimed in claim 13, wherein said washing station includes means for withdrawing by suction any residual liquid in the reaction tube when the tube is moved by said turntable into a first given position, means for rinsing the reaction tube with rinsing liquid when the tube is moved into a second given position, and means for drying the tube when the tube is moved into a third given position.

15. An automatically operating analysis apparatus for analysing liquid samples, comprising
a rotatable turntable;
a plurality of reaction tubes carried by said turntable and means to uniformly spaced said tubes around the periphery of said turntable;
a sample supply station;
at least first and second reagent supply stations;
a measuring station;
means to locate said sample supply station, said first and second reagent supply stations and said measuring station at separate locations around the periphery of said turntable;
said sample supply station including holder means for holding a plurality of sample containers for a respective liquid sample each and sample transfer means including a metering pump having a suction tube and being operative to draw liquid into said suction tube by suction and to dispense said liquid in an accurately determined volume;
means to controllably move said suction tube to positions above said sample containers for selective removal by suction of sample liquid from any one of said sample containers and to controllably move said suction tube to a position above one of said reaction tubes which is moved by said turntable into a given position relative to the sample supply station for dispensing sample liquid into said reaction tube;
each of said first and second reagent supply stations including a plurality of stationary reagent supply cups for a respective reagent liquid each and reagent transfer means including a metering pump having a suction tube operative to draw liquid into said suction tube by suction and to dispense said liquid in an accurately determined volume;
means to controllably move said last mentioned suction tube to positions above said stationary reagent cups for selective removal by suction of reagent liquid from any one of said cups and to controllably move said suction tube to positions above either one of two different reaction tubes moved by said turntable into two different given positions relative to the reagent supply station for dispensing reagent liquid into either one of said two reaction tubes;
said measuring station including measuring means for analytically measuring a given property of a sample held in one of said reaction tubes; and
drive means for stepwise rotating said turntable through rotation steps corresponding alternatingly to m and n angular spacings between two adjacent reaction tubes, where m and n are different whole numbers, and the number of said reaction tubes is not divisible by the sum m+n;
means to cause each reaction tube to be moved by said turntable through a plurality of complete turns of the turntable before the liquid present in said reaction tube is subjected to an analytical measuring operation by said measuring means; whereby each reaction tube during said plurality of complete turns of said turntable is at least twice brought to the same position relative to said sample supply station and each of said first and second reagent supply stations, respectively; and
said last mentioned means to cause permitting sample liquid and reagent liquid, respectively, to be transferred to said reaction tube and also permitting said sample supply station and each of said first and second reagent supply stations to transfer sample liquid and reagent liquid, respectively, to each separate reaction tube at at least two different occasions prior to liquid in said reaction tube being subjected to a measuring operation in said measuring station.

16. An apparatus as claimed in claim 15, means to locate at least one reagent supply station after said sample supply station but before said measuring station as seen in the direction of rotation of said turntable, and means to locate at least one other reagent supply station before said sample supply station but after said measuring station as seen in the direction of rotation of said turntable.

17. An apparatus as claimed in claim 15, wherein each of said reagent supply stations also includes a stationary wash cup for a washing liquid and a stationary waste outlet, and means to controllably move said suction tube of said metering pump to a position above said wash cup for withdrawing liquid therefrom by suction and to another position above said waste outlet for emptying the contents of the pump thereinto.

18. An apparatus as claimed in claim 15, and means to move said suction tube of said metering pump in each reagent supply station in a circular path along which circular path said stationary reagent cups are located and which extends above two different reaction tubes carried by said turntable.

19. An apparatus as claimed in claim 15, and means to move said suction tube of said metering pump in said sample supply station in a rectilinear path, and said holder means comprise means for holding a plurality of rows of sample containers extending mutually parallel and parallel with the movement path of said suction tube, and means to controllably move said holder means so as to selectively place any one of said rows of sample containers in alignment with the path of movement of said suction tube.

20. An apparatus as claimed in claim 15, wherein said sample supply station also includes a stationary wash cup for a washing liquid and a stationary waste outlet, means to controllably move said suction tube of said metering pump in the sample supply station to a position above said wash cup for withdrawing washing liquid by suction therefrom and to another position above said waste outlet for emptying its contents into said waste outlet.

21. An apparatus as claimed in claim 15, said measuring station including suction means for withdrawing liquid from a said reaction tube when said reaction tube is moved by said turntable into said given position relative the measuring station and for transferring said withdrawn liquid to said measuring means, and said measuring means comprising several independent, sequentially operative measuring channels to which liquids withdrawn by said suction means from reaction tubes move sequentially into said given position are transferred.

22. An apparatus as claimed in claim 15, including a washing station, means to locate said washing station at the periphery of said turntable after said measuring station, as seen in the direction of rotation of said turntable, and before said reagent supply station, said washing station including means for withdrawing by suction any residual liquid in a reaction tube moved by said turntable into a first given position, means for rinsing said reaction tube with rinsing liquid when moved into a second given position, and means for drying said tube when moved into a third given position.

* * * * *